United States Patent
Beidleman et al.

(10) Patent No.: US 11,642,052 B2
(45) Date of Patent: May 9, 2023

(54) SYSTEMS AND METHODS FOR MONITORING SUBJECTS IN POTENTIAL HYPOXIC DISTRESS

(71) Applicant: THE GOVERNMENT OF THE UNITED STATES, AS REPRESENTED BY THE SECRETARY OF THE ARMY, Fort Detrick, MD (US)

(72) Inventors: Beth Beidleman, Holliston, MA (US); Mark Buller, Douglas, MA (US); Alexander Welles, Brookline, MA (US)

( * ) Notice: Subject to any disclaimer, the term of this patent is extended or adjusted under 35 U.S.C. 154(b) by 645 days.

(21) Appl. No.: 16/628,158

(22) PCT Filed: Dec. 8, 2018

(86) PCT No.: PCT/US2018/064637
§ 371 (c)(1),
(2) Date: Jan. 2, 2020

(87) PCT Pub. No.: WO2019/113562
PCT Pub. Date: Jun. 13, 2019

(65) Prior Publication Data
US 2020/0146602 A1    May 14, 2020

Related U.S. Application Data

(60) Provisional application No. 62/596,511, filed on Dec. 8, 2017.

(51) Int. Cl.
*A61B 5/00* (2006.01)
*A61B 5/1455* (2006.01)
(Continued)

(52) U.S. Cl.
CPC ............ *A61B 5/14551* (2013.01); *A61B 5/02* (2013.01); *A61B 5/08* (2013.01); *A61B 5/11* (2013.01);
(Continued)

(58) Field of Classification Search
CPC ......... A61B 5/14551; A61B 5/02; A61B 5/08; A61B 5/11; A61B 5/22; A61B 5/4023; A61B 5/7275; A61M 16/12; G16H 50/30
See application file for complete search history.

(56) References Cited

U.S. PATENT DOCUMENTS 9,492,084 B2   11/2016   Behar et al.
9,788,797 B2   10/2017   Rouquette
(Continued)

FOREIGN PATENT DOCUMENTS

CN    105212945 A    1/2016

OTHER PUBLICATIONS

Beidleman, Beth; Welles, Alexander; Buller, Mark, Predicting individual risk of altitude illness using real-time monitoring of accumulated hypoxic debt, Journal of Science and Medicine in Sport, vol. 20, Supp. 2, Nov. 2017.
(Continued)

*Primary Examiner* — May A Abouelela
(74) *Attorney, Agent, or Firm* — Leigh Z. Callander

(57) ABSTRACT

A method of monitoring a subject for the risk of Acute Mountain Sickness (AMS) includes obtaining real-time pulse arterial oxygen saturation (SpO$_2$) measurements from the subject. The SpO$_2$ measurements are transformed into a novel metric known as Accumulated Hypoxic Debt (AHD). The AHD metric is used as the independent variable in a longitudinal generalized linear mixed model to calculate the probability D that the subject is at risk of AMS. Based on the probability D, appropriate courses of action may be com-
(Continued)

municated to the subject via the output device of a wearable or portable monitor.

22 Claims, 1 Drawing Sheet

(51) Int. Cl.
    *A61B 5/02*     (2006.01)
    *A61B 5/08*     (2006.01)
    *A61B 5/11*     (2006.01)
    *A61B 5/22*     (2006.01)
    *A61M 16/12*     (2006.01)

(52) U.S. Cl.
    CPC .............. *A61B 5/22* (2013.01); *A61B 5/4023* (2013.01); *A61B 5/7275* (2013.01); *A61M 16/12* (2013.01)

(56) References Cited

U.S. PATENT DOCUMENTS

| | | | |
|---|---|---|---|
| 10,561,863 B1* | 2/2020 | Dashevsky | A61B 5/01 |
| 10,786,693 B1* | 9/2020 | Opperman | A61B 5/0873 |
| 10,980,491 B1* | 4/2021 | Jones | G16H 15/00 |
| 11,103,159 B2* | 8/2021 | Harshman | A61B 5/0833 |
| 2004/0206352 A1* | 10/2004 | Conroy, Jr. | A61B 5/14551 |
| | | | 128/204.23 |
| 2004/0206353 A1* | 10/2004 | Conroy, Jr. | A61B 5/14551 |
| | | | 128/204.23 |
| 2006/0281996 A1 | 12/2006 | Kuo et al. | |
| 2012/0245439 A1 | 9/2012 | Andre et al. | |
| 2013/0038459 A1* | 2/2013 | Abe | A61B 5/6898 |
| | | | 340/686.1 |
| 2013/0325498 A1 | 12/2013 | Muza, Jr. | |
| 2014/0129008 A1 | 5/2014 | Utter, II | |
| 2014/0142970 A1 | 5/2014 | Baronov et al. | |
| 2014/0316287 A1 | 10/2014 | Watson et al. | |
| 2015/0250417 A1 | 9/2015 | Cheng et al. | |
| 2015/0265170 A1 | 9/2015 | Wisloff et al. | |
| 2016/0324488 A1 | 11/2016 | Olsen | |
| 2016/0367183 A1 | 12/2016 | Miyasaka | |
| 2017/0020446 A1 | 1/2017 | Warren et al. | |
| 2017/0251962 A1* | 9/2017 | Shiho | A61B 5/0205 |
| 2017/0265817 A1 | 9/2017 | Takamatsu et al. | |
| 2017/0268796 A1 | 9/2017 | Takahashi | |
| 2017/0325727 A1* | 11/2017 | Buza | A61B 5/742 |
| 2018/0132768 A1* | 5/2018 | Sasahara | A61B 5/14551 |
| 2018/0174686 A1 | 6/2018 | Zaphrir et al. | |

OTHER PUBLICATIONS

PCT International Search Report and Written Opinion, dated Feb. 8, 2019.

* cited by examiner

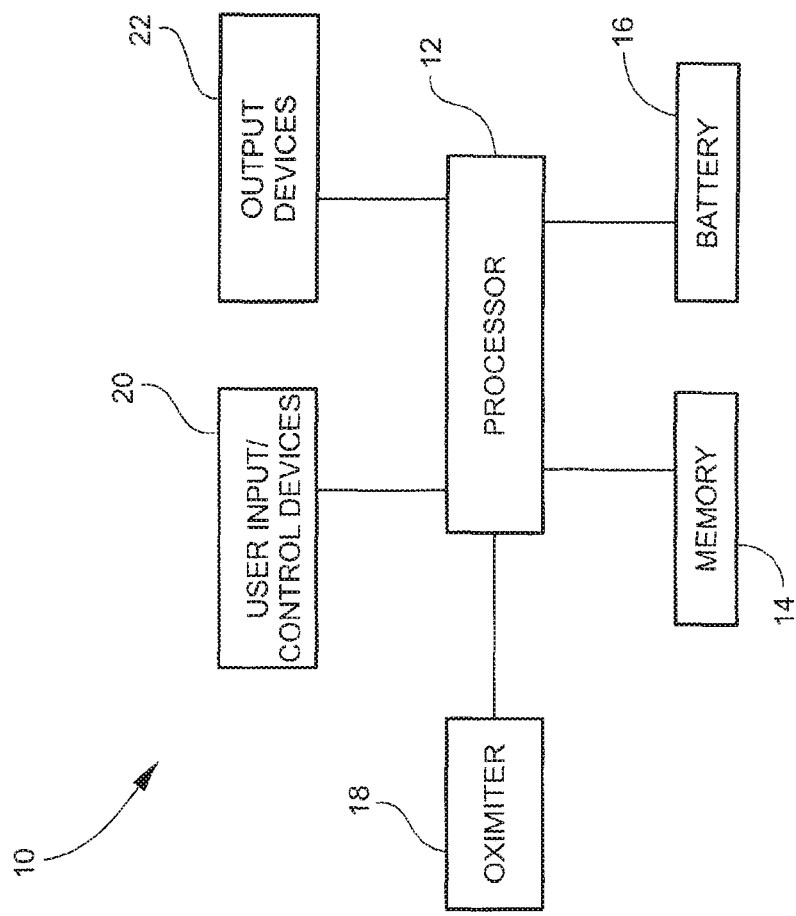

SYSTEMS AND METHODS FOR MONITORING SUBJECTS IN POTENTIAL HYPOXIC DISTRESS

CROSS REFERENCE TO RELATED APPLICATIONS

The present application claims the benefit of priority of U.S. provisional patent application Ser. No. 62/596,511 filed on Dec. 8, 2017, which is expressly incorporated by reference herein.

STATEMENT OF GOVERNMENT INTEREST

The invention described herein may be manufactured, used and licensed by or for the United States Government.

BACKGROUND OF THE INVENTION

The invention relates in general to altitude illness and in particular to Acute Mountain Sickness (AMS).

Acute mountain sickness (AMS) is the most common altitude illness and its symptoms include headache, nausea, fatigue, decreased appetite, and poor sleep [1, 2]. (Note: The bracketed numbers at the end of a sentence refer to the references listed at the end of the specification). The number of individuals who suffer from AMS rises in direct proportion to the ascent rate and elevation [3, 4]. Unacclimatized lowlanders can experience 70-80% incidence of AMS with 40-50% having moderate to severe symptoms with rapid ascent to 4300 meters [3]. When AMS symptoms are severe, individuals can be completely incapacitated and unable to perform the simplest of tasks [5]. Large decrements in both physical and cognitive performance also occur with rapid ascent to high altitude [6-8]. Research has reported that endurance performance in events lasting 1-3 hours is impaired by 10-15% at 3000 meters and 40-80% at 4300 meters in unacclimatized lowlanders following rapid ascent [9, 10].

Research has also demonstrated that cognitive performance is impacted by 20-50% following rapid ascent to high altitudes, depending on the altitude, with unlearned complex activities affected more than well-learned simple activities [11-14]. Warfighters who are rapidly deployed to altitude may suffer from symptoms of AMS. Some security analyses conclude that there are 60 world-wide high altitude areas for possible U.S. military engagement. In addition, it is estimated that over 100 million people annually visit areas of high altitude for recreation, work and travel.

Despite decades of research, individualized real-time predictors of decrements in health and performance while visiting or residing at altitude are lacking. The clinical definition of hypoxia is pulse arterial oxygen saturation below 90%. Although technology to measure pulse arterial oxygen saturation ($SpO_2$) has existed for years, single point measurements of $SpO_2$ have not been able to predict the occurrence of AMS or decrements in physical and cognitive performance. There are currently no real-time, individualized technical methods to predict the likelihood of hypoxic events and altitude acclimatization status.

In one known technique, once an individual is at altitude, a self-assessment questionnaire (for example, the Lake Louise Scoring System) may be used to determine if the individual has AMS. The self-assessment questionnaires are not particularly helpful for predicting the risk of AMS in real-time before it occurs. In addition, completing the questionnaire requires that the individual stop his/her current activity and devote time to assessing his/her physical and mental conditions. A need exists for a technical solution that can predict the likelihood of AMS in real-time on an individual basis, without requiring the individual to interrupt his/her activities and consume valuable time.

SUMMARY OF THE INVENTION

One aspect of the invention is a method for real-time monitoring of an individual. The method may include: (a) providing a pulse arterial oxygen saturation ($SpO_2$) sensor and a portable computing device to an individual; (b) using the sensor, measuring the $SpO_2$ value of the individual in real-time once a second; (c) using a processor in the computing device, obtaining an average real-time $SpO_2$ value over a time interval between 1 and 60 seconds; (d) using the processor, subtracting the average real-time $SpO_2$ value from 90% to obtain a real-time $SpO_2$ difference; (e) using the processor, multiplying the real-time $SpO_2$ difference by the time interval and converting the product to % hours to obtain a real-time hypoxic debt value; (f) storing the real-time hypoxic debt value in a memory of the computing device; (g) repeating steps (b)-(f) for a plurality of the time intervals; (h) using the processor, retrieving a plurality of stored real-time hypoxic debt values from the memory; (i) using the processor, summing the plurality of retrieved real-time hypoxic debt values to obtain accumulated hypoxic debt (AHD); (j) using the processor, calculating a probability (D) of experiencing acute mountain sickness as $D = e^{-1.94 + 0.017(AHD)} / 1 + e^{-1.94 + 0.017(AHD)}$; and (k) using an output device, communicating the probability D to the individual.

Step (b) may include measuring the $SpO_2$ value of the individual in real-time when the individual is located above an altitude of about 2500 meters.

Step (c) may include using the processor to obtain an average real-time $SpO_2$ value over a time interval of 15 seconds.

Step (e) may include using the processor to multiply the real-time $SpO_2$ difference by the time interval of 15 seconds and converting the product to % hours to obtain a real-time hypoxic debt value.

Step (g) may include repeating steps (b)-(f) for a plurality of the 15 second time intervals.

Steps (b)-(k) may be repeated over a period of 48 hours.

Step (k) may include communicating the probability D to the individual using a visual display. Step (k) may include using the output device to communicate a course of action to the individual. Step (k) may include communicating one or more of the probability D and the course of action in one or more of a numerical format, a color-coded format and a format using words.

Another aspect of the invention is a non-transitory computer-readable medium with instructions stored thereon that, when executed by a processor, a memory, a pulse arterial oxygen saturation ($SpO_2$) sensor, and an output device, perform the steps comprising steps (b)-(k) recited above.

A further aspect of the invention is a system for real-time monitoring of an individual for a risk of Acute Mountain Sickness. The system may include a pulse arterial oxygen saturation ($SpO_2$) sensor configured to extract $SpO_2$ measurements from the individual and a portable computing device configured to be worn or carried by the individual and connected to the $SpO_2$ sensor. The portable computing device may include a processor, a memory, and an output device.

The processor may be configured to (a) obtain an average real-time $SpO_2$ value over a 15 second time interval; (b)

subtract the average real-time $SpO_2$ value from 90% to obtain a real-time $SpO_2$ difference; (c) multiply the real-time $SpO_2$ difference by the time period of 15 seconds and convert the product to % hours to obtain a real-time hypoxic debt value; (d) store the real-time hypoxic debt value in the memory of the computing device; (e) retrieve a plurality of stored real-time hypoxic debt values from the memory; (f) sum the plurality of retrieved real-time hypoxic debt values to obtain accumulated hypoxic debt (AHD); (g) calculate a probability (D) of experiencing acute mountain sickness as $D=e^{-1.94+0.017(AHD)}/1+e^{-1.94+0.017(AHD)}$; and (h) communicate the probability D to the individual by sending the probability D to the output device.

In another aspect of the invention, a method of detecting Acute Mountain Sickness (AMS) in a human includes obtaining $SpO_2$ measurements from the human; detecting whether the human is at risk of AMS by transforming the $SpO_2$ measurements to accumulated hypoxic debt (AHD); and using the AHD as an independent variable in a longitudinal generalized linear mixed model to calculate the probability D that the human is at risk of AMS.

The probability D may equal $e^{-1.94+0.017(AHD)}/1+e^{-1.94+0.017(AHD)}$.

The invention will be better understood, and further objects, features and advantages of the invention will become more apparent from the following description, taken in conjunction with the accompanying drawings.

BRIEF DESCRIPTION OF THE DRAWINGS

In the drawings, which are not necessarily to scale, like or corresponding parts are denoted by like or corresponding reference numerals.

The single FIGURE is a schematic diagram of one embodiment of an individualized hypoxia monitor.

DETAILED DESCRIPTION

A novel apparatus and method utilizes real-time monitoring and analysis of an individual's pulse arterial oxygen saturation ($SpO_2$) to predict the risk of the occurrence of Acute Mountain Sickness (AMS) during the first 48 hours at altitude (above 2500 meters). For soldiers, the first 48 hours at altitude is the riskiest. A novel, useful, unconventional and non-routine metric is "accumulated hypoxic debt (AHD)" in units of % hours.

To determine an individual's AHD, first, an individual's real-time $SpO_2$ is measured by a sensor worn by the individual. The real-time $SpO_2$ may be measured, for example, once a second. The measured real-time $SpO_2$ is then averaged across a relatively short time interval to obtain an average real-time $SpO_2$ measurement for that short time interval. In one embodiment, the short time interval is 15 seconds. In other embodiments, the short time interval may be longer or shorter than 15 seconds.

The $SpO_2$ difference is 90% minus the average real-time $SpO_2$ calculated over the short time interval. The $SpO_2$ difference is then multiplied by the length of the short time interval (for example, 15 seconds (15/3600 hours)) to obtain a single hypoxic debt amount in % hours. Then, the single hypoxic debt amounts are summed over the total time interval during which $SpO_2$ measurements have been taken to thereby obtain the AHD in % hours.

The AHD is then used in a longitudinal generalized linear mixed model to assess the risk of experiencing AMS. The preferred model is of the form shown in Equation 1. below:

$$y_i = \sum_{j=0}^{M} \beta_j x_{ij} + \varepsilon_i.$$
Equation 1

In the model, x is the real-time measured AHD. The AHD is used to calculate y, which is the risk of experiencing AMS. The model was developed using sixteen healthy nonsmoking unacclimatized lowlanders (M=11, F=5, age=23±6 yrs, weight=74±13 kg; mean±SD) that ascended to the summit of Pikes Peak (PP) at 4300 meters and wore a physiologic status monitor (Equivital™ EQ-02) that measured pulse arterial oxygen saturation ($SpO_2$) every 15 seconds for the first 20 hours of altitude exposure. An Environmental Symptoms Questionnaire was utilized to measure the prevalence and severity of AMS after 4, 8, 12 and 20 hours of exposure. Data was filtered such that all volunteers had the same number of physiologic measurements. AHD (% hr) was calculated by multiplying the real-time $SpO_2$ difference [90%−actual $SpO_2$] by the time period (15 sec), converting this to % hours of hypoxic debt and then summing the hypoxic debt amounts over the total time period.

In Equation 1., the regression coefficient β equals 0.017 and the residual variable ε equals −1.94. Thus, the percent probability D of experiencing AMS is given by Equation 2. below:

$$D=(e^{-1.94+0.017(AHD)})/(1+e^{-1.94+0.017(AHD)})$$
Equation 2.

AHD was a significant predictor (P=0.002) of the occurrence of AMS over time at altitude. Every 10% hour increase in AHD increased the odds of getting AMS by 18.4% (odds ratio, 1.184; confidence interval, 1.065-1.316) [16]. The model has been externally validated in a set of ten volunteers exposed to either 3000 meters or 4000 meters and had the ability to correctly diagnose AMS 86% of the time during the first 24 hours of altitude exposure.

Using the model, Table 1. below shows the risk (%) of Acute Mountain Sickness calculated from Accumulated Hypoxic Debt (AHD) (% hr). The bracketed ranges are the 95% confidence intervals.

TABLE 1

| Accumulated Hypoxic Debt (% hr) | Risk of AMS (%) |
| --- | --- |
| 10 | 18.4 [6.5-31.6] |
| 20 | 40.2 [13.4-73.3] |
| 30 | 66.0 [20.7-228.0] |
| 40 | 196 [128-300] |
| 50 | 232 [137-395] |
| 60 | 275 [145-520] |

A very important benefit of the novel, unconventional, non-routine hypoxic debt metric is its universal nature. For instance, it can be utilized at any altitude. Individuals will accumulate more hypoxic debt the higher the altitude and less hypoxic debt the lower the altitude. In addition, it can be utilized in men and women. Women tend to demonstrate higher $SpO_2$ measurements at altitude and AHD takes that variability into account. The metric also takes into account the desaturation that occurs with physical activity at altitude. Individuals engaging in vigorous physical activity experience a 5%-10% desaturation depending on the altitude, which effectively puts individuals at a higher altitude for a given period of time. Heavy physical exercise at altitude, therefore, is typically associated with higher values of AMS. In addition, medication, such as acetazolamide, stimulates ventilation, which is accounted for by the hypoxic debt metric. Last, this hypoxic debt metric captures the importance of AHD over time at altitude. Individuals do not immediately experience AMS upon arrival at altitude. AMS develops after about 4 hours of altitude exposure, peaks around 18-22 hours of exposure and then subsides after 36 hours of exposure. The real-time component of the hypoxic debt metric is useful in tracking the time course of AMS.

FIG. 1 is a schematic diagram of one embodiment of an individualized hypoxia monitor or apparatus 10. Embodiments of the apparatus 10 may include a portable computing device, for example, a wrist-worn device and/or a smartphone. Apparatus 10 either includes or is in communication with an oximeter ($SpO_2$ sensor) 18. Sensor 18 is connected to a processor 12. Memory 14 and battery 16 (or other power supply) are connected to the processor 12. User input and control devices 20 and output devices 22 are connected to the processor 12. The user input and control devices 20 may include, for example, keyboards (virtual or real), touch screens, microphones, movable switches, ports and jacks, such as USB ports, memory card slots, such as SD card slots, etc. Output devices 22 may include, for example, visual displays, speakers, vibrating devices, antennas, ports and jacks, such as USB ports, memory card slots, such as SD card slots, etc.

Suitable $SpO_2$ sensors 18 are available from, for example, Equivital, Inc., Cambridge, UK; Athena GTX, Des Moines, Iowa: Masimo, Inc., Irvine, Calif.; and Nonin, Inc., Plymouth, Minn. These companies may also provide portable and/or wearable devices that incorporate the required capabilities of processor 12, memory 14, battery 16 and input and output devices 20, 22. Many currently available smart phones models would also be suitable and can be connected to sensor 18 wirelessly via a Bluetooth® connection.

It is not necessary that the user input any information into apparatus 10 other than the real-time $SpO_2$ measurements provided by sensor 18. Using the real-time $SpO_2$ measurements, the processor 12 calculates the AHD and then uses the AHD to calculate the probability D of experiencing AMS using Equation 2. It is important to note that even if a human being could manually perform the calculations performed by the processor 12, the time required to manually calculate the real-time AHD at small time intervals, such as 15 seconds, and then manually calculate the probability D of experiencing AMS using Equation 2 would be prohibitive and would so interfere with the individual's other activities as to make doing so virtually worthless. Thus, a computer processor is a necessary and integral component of apparatus 10.

Apparatus 10 may provide the probability D to the user via an output device 22, such as a visual display. In addition, the apparatus 10 may provide a visual indication of the category of the probability D, such as MILD, MODERATE, or SEVERE, for example. In addition to or as a substitute for a textual display, apparatus 10 may visually display a color code, such as green for MILD, yellow for MODERATE, or red for SEVERE. In some embodiments, apparatus 10 may provide instructions and appropriate courses of action to the individual, for example, on a visual display. For example, if the probability D is less than 30%, then a message such as "CONTINUE ACTIVITIES" may be displayed. If D is more than 30% but less than 50%, then a message such as "STOP ASCENDING" may be displayed. If D is more than 50%, then a message such as "DESCEND IMMEDIATELY" may be displayed. When AHD is 64.3 hours, then the probability D is greater than 30%. In one embodiment, if the probability D is greater than 30%, then a change in the individual's level of activity is indicated. Other instructions and other ranges of probabilities may be used.

For example, if the individual has a probability D between a first threshold and a second threshold that is greater than the first threshold (for example, between 30% and 50%), then the individual may be treated by stopping the individual from ascending to a higher elevation. In addition, if the individual has a probability D between the first threshold and the second threshold, the individual may be further treated by administering acetazolamide and/or administering oxygen therapy. If the individual has a probability D greater than the second threshold, the individual may be treated by moving the individual to a lower elevation.

Embodiments of the invention have been described to explain the nature of the invention. Those skilled in the art may make changes in the details, materials, steps and arrangement of the described embodiments within the principle and scope of the invention, as expressed in the appended claims.

REFERENCE LIST

1. Roach, R. C., et al., *The Lake Louise Acute Mountain Sickness scoring system*, in *Hypoxia and Molecular Medicine*, J. R. Sutton, C. S. Houston, and G. Coates, Editors. 1993, Queen City Printers: Burlington. p. 272-274.
2. Hackett, P. H. and R. C. Roach, *High altitude illness*. N. Engl. J. Med, 2001. 345(2): p. 107-114.
3. Beidleman, B. A., et al., *Predictive models of acute mountain sickness after rapid ascent to various altitudes*. Med. Sci. Sports Exerc, 2013. 45(4): p. 792-800.
4. Hackett, P. H., D. Rennie, and H. D. Levine, *The incidence, importance, and prophylaxis of acute mountain sickness*. Lancet, 1976. 2(7996): p. 1149-1154.
5. Roach, R., J. Stapanek, and P. Hackett, *Acute mountain sickness and high-altitude cerebral edema*, in *Medical Aspects of Harsh Environments, Volume 2*, K. B. Pandolf and R. E. Burr, Editors. 2002, Associated Press: New York. p. 765-793.
6. Maher, J. T., L. G. Jones, and L. H. Hartley, *Effects of high altitude exposure on submaximal endurance capacity of man*. J. Appl. Physiol, 1974. 37(6): p. 895-898.
7. Horstman, D., R. Weiskopf, and R. E. Jackson, *Work capacity during 3-wk sojourn at 4,300 m: effects of relative polycythemia*. J. Appl. Physiol, 1980. 49(2): p. 311-318.
8. Fulco, C. S., et al., *Carbohydrate supplementation improves cycle time-trial performance during energy deficit at 4,300-m altitude*. J. Appl. Physiol, 2005. 99(3): p. 867-876.
9. Beidleman, B. A., et al., *Quantitative model of sustained physical task duration at varying altitudes*. Med. Sci. Sports Exerc, 2015. September 3((epub ahead of print)).
10. Fulco, C. S. and A. Cymerman, *Physical performance at varying terrestrial altitudes*, in *Medical Aspects of Harsh Environments, Volume 2*, D. E. Lounsbury, R. F. Bellamy, and R. Zatchuk, Editors. 2002, Borden Institute: Washington, D.C. p. 693-728.
11. Subudhi, A. W., et al., *AltitudeOmics: The integrative physiology of human acclimatization to hypobaric hypoxia and its retention upon reascent*. PLoS One, 2014. 9(3): p. e92191.
12. Kryskow, M. A., et al., *Performance during simple and complex military psychomotor tasks at various altitudes*. Aviat. Space Environ. Med, 2013. 84(9): p. 1-6.
13. Beidleman, B. A., et al., *Is normobaric hypoxia an effective treatment for sustaining previously acquired altitude acclimatization*. J. Appl. Physiol, 2017. 123: p. 1214-1227.

14. Banderet, L. E. and B. Shukitt-Hale, *Cognitive performance, mood, and neurological status at high terrestrial elevations*, in *Medical aspects of harsh environments*, D. E. Lounsbury, R. F. Bellamy, and R. Zajtchuk, Editors. 2002, Office of the Surgeon General: Washington, D.C. p. 729-763.
15. Beidleman, B. A., et al., *Quantitative Model of Sustained Physical Task Performance at Varying Altitudes*. Med. Sci. Sports Exerc., 2015. 48: p. 323-30.
16. Beidleman, B. A., A. P. Welles, and M. J. Buller, *Predicting individual risk of altitude illness using real-time monitoring of accumulated hypoxic debt*. J. Sci. Med. Sport, 2017. 20: p. S94-S95.

What is claimed is:

1. A method of detecting and treating Acute Mountain Sickness (AMS) in an individual, comprising:
    determining accumulated hypoxic debt (AHD) of the individual;
    determining a probability D that the individual has AMS, based on the AHD;
    if the individual has the probability D between a first threshold and a second threshold that is greater than the first threshold, then treating the individual by stopping the individual from ascending to a higher elevation; and
    if the individual has the probability D greater than the second threshold, then treating the individual by moving the individual to a lower elevation.

2. The method of claim 1 wherein, if the individual has the probability D between the first threshold and the second threshold, further treating the individual by administering acetazolamide.

3. The method of claim 1 wherein, if the individual has the probability D between the first threshold and the second threshold, further treating the individual by administering oxygen therapy.

4. A system for detecting a risk of Acute Mountain Sickness (AMS) in an individual, comprising:
    a pulse arterial oxygen saturation ($SpO_2$) sensor configured to extract $SpO_2$ measurements from the individual; and
    a portable computing device configured to be worn or carried by the individual and connected to the $SpO_2$ sensor;
    the portable computing device including a processor, a memory, and an output device wherein the processor determines accumulated hypoxic debt (AHD) and a probability D that the individual has AMS based on the AHD, and compares the probability D to a first threshold to determine if treatment is needed.

5. The system of claim 4, wherein the processor communicates the treatment to the individual via the output device.

6. The system of claim 5, wherein, if the individual has the probability D between the first threshold and a second threshold that is greater than the first threshold, then the treatment is stopping the individual from ascending to a higher elevation; and if the individual has the probability D greater than the second threshold, then the treatment is moving the individual to a lower elevation.

7. The system of claim 6 wherein, if the individual has the probability D between the first threshold and the second threshold, then the treatment is additionally administering acetazolamide to the individual.

8. The system of claim 6, wherein, if the individual has the probability D between the first threshold and the second threshold, then the treatment is additionally administering oxygen therapy to the individual.

9. The system of claim 4, wherein determining accumulated hypoxic debt (AHD) includes (a) obtaining an average real-time $SpO_2$ value over a 15 second time interval; (b) subtracting the average real-time $SpO_2$ value from 90% to obtain a real-time $SpO_2$ difference; (c) multiplying the real-time $SpO_2$ difference by the time interval of 15 seconds and converting the result to percent hours to obtain a real-time hypoxic debt value; (d) storing the real-time hypoxic debt value in the memory of the portable computing device; (e) retrieving a plurality of stored real-time hypoxic debt values from the memory; and (f) summing the plurality of retrieved real-time hypoxic debt values to obtain accumulated hypoxic debt (AHD).

10. The system of claim 4, wherein determining the probability D that the individual has AMS includes calculating the probability D from the relationship $D = e^{-1.94+0.017(AHD)}/1 + e^{-1.94+0.017(AHD)}$.

11. A method of detecting Acute Mountain Sickness (AMS) in a human, comprising:
    obtaining $SpO_2$ measurements from the human;
    detecting whether the human is at risk of AMS by transforming the $SpO_2$ measurements to accumulated hypoxic debt (AHD); and
    using the AHD as an independent variable in a longitudinal generalized linear mixed equation to calculate the probability D that the human is at risk of AMS.

12. The method of claim 11, wherein the probability D equals $e^{-1.94+0.017(AHD)}/1 + e^{-1.94+0.017(AHD)}$.

13. A method for real-time monitoring of an individual to determine a probability that the individual will contract acute mountain sickness (AMS), comprising:
    (a) providing a pulse arterial oxygen saturation ($SpO_2$) sensor and a portable computing device to the individual;
    (b) using the sensor, measuring an $SpO_2$ value of the individual in real-time once a second;
    (c) using a processor in the portable computing device, obtaining an average real-time $SpO_2$ value over a time interval between 1 and 60 seconds;
    (d) using the processor, subtracting the average real-time $SpO_2$ value from 90% to obtain a real-time $SpO_2$ difference;
    (e) using the processor, multiplying the real-time $SpO_2$ difference by the time interval and converting the result to percent hours to obtain a real-time hypoxic debt value;
    (f) storing the real-time hypoxic debt value in a memory of the portable computing device;
    (g) repeating steps (b)-(f) for a plurality of the time intervals;
    (h) using the processor, retrieving a plurality of stored real-time hypoxic debt values from the memory;
    (i) using the processor, summing the plurality of retrieved real-time hypoxic debt values to obtain accumulated hypoxic debt (AHD);
    (j) using the processor, calculating a probability (D) of experiencing acute mountain sickness as $D = e^{-1.94+0.017(AHD)}/1 + e^{-1.94+0.017(AHD)}$; and
    (k) using an output device, communicating the probability D to the individual.

14. The method of claim 13, wherein step (b) includes measuring the $SpO_2$ value of the individual in real-time when the individual is located above an altitude of about 2500 meters.

15. The method of claim 13, wherein step (c) includes using the processor to obtain an average real-time $SpO_2$ value over a time interval of 15 seconds.

16. The method of claim 15, wherein step (e) includes using the processor to multiply the real-time $SpO_2$ difference by the time interval of 15 seconds and converting the result to percent hours to obtain a real-time hypoxic debt value.

17. The method of claim 16, wherein step (g) includes repeating steps (b)-(f) for a plurality of the 15 second time intervals.

18. The method of claim 17, wherein steps (b)-(k) are repeated over a period of 48 hours.

19. The method of claim 13, wherein step (k) includes communicating the probability D to the individual using a visual display.

20. The method of claim 19, wherein step (k) includes using the output device to communicate a treatment to the individual.

21. The method of claim 20, wherein step (k) includes communicating one or more of the probability D and the treatment in one or more of a numerical format, a color-coded format and a format using words.

22. A non-transitory computer-readable medium with instructions stored thereon that, when executed by a processor, a memory, a pulse arterial oxygen saturation ($SpO_2$) sensor, and an output device, perform the steps comprising steps (b)-(k) of claim 13.

* * * * *